United States Patent
Silcock et al.

(10) Patent No.: US 12,403,136 B2
(45) Date of Patent: Sep. 2, 2025

(54) CANNABINOID DERIVATIVES AS PHARMACEUTICALLY ACTIVE COMPOUNDS AND METHODS OF PREPARATION THEREOF

(71) Applicant: JAZZ PHARMACEUTICALS RESEARCH UK LIMITED, Sittingbourne (GB)

(72) Inventors: Alan Silcock, Cambridge (GB); Benjamin Whalley, Cambridge (GB); Royston Gray, Cambridge (GB); Hannah Straker, Cambridge (GB); Karen Tse, Cambridge (GB); Alexander Cobb, London (GB); Laura Bryant, Leigh-on-Sea (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 783 days.

(21) Appl. No.: 17/627,946

(22) PCT Filed: Jul. 17, 2020

(86) PCT No.: PCT/GB2020/051723
§ 371 (c)(1),
(2) Date: Jan. 18, 2022

(87) PCT Pub. No.: WO2021/014132
PCT Pub. Date: Jan. 28, 2021

(65) Prior Publication Data
US 2022/0288055 A1    Sep. 15, 2022

(30) Foreign Application Priority Data
Jul. 19, 2019    (GB) .................... 1910389

(51) Int. Cl.
*A61K 31/47*    (2006.01)
*A61K 31/05*    (2006.01)
(Continued)

(52) U.S. Cl.
CPC .............. *A61K 31/47* (2013.01); *A61K 31/05* (2013.01); *A61K 31/055* (2013.01);
(Continued)

(58) Field of Classification Search
CPC .......... A61K 31/47; A61P 25/08; C07C 37/16
(Continued)

(56) References Cited

U.S. PATENT DOCUMENTS 8,632,825 B2    1/2014   Velasco Diez et al.
8,790,719 B2    7/2014   Parolaro et al.
(Continued)

FOREIGN PATENT DOCUMENTS

EP          3 061 450 A1    8/2016
WO     WO 01/95899 A2    12/2001
(Continued)

OTHER PUBLICATIONS

Namba K, Yamamoto H, Sasaki I, Mori K, Imagawa H, Nishizawa M. Hg (OTf) 2-catalyzed arylene cyclization. Organic Letters. May 1, 2008;10(9):1767-70. (Year: 2008).*
(Continued)

*Primary Examiner* — Jeffrey S Lundgren
*Assistant Examiner* — Heather Dahlin
(74) *Attorney, Agent, or Firm* — COOLEY LLP

(57) ABSTRACT

The present invention relates to a group of cannabinoid derivatives as pharmaceutically active compounds and methods of preparation thereof. The cannabinoid derivatives of the invention are analogues of cannabidiol (CBD). CBD is a non-psychoactive cannabinoid which has been used to treat various diseases and disorders. While such treatments (Continued)

Effect of Compound 12a on the electroshock-induced generalised seizure threshold (MEST) in the mouse hold promise, there remains a need in the art for more effective treatments and this has been brought about by way of the cannabinoid derivatives of the invention

13 Claims, 4 Drawing Sheets

(51) Int. Cl.

| | |
|---|---|
| *A61K 31/055* | (2006.01) |
| *A61K 31/353* | (2006.01) |
| *A61K 45/06* | (2006.01) |
| *A61P 25/08* | (2006.01) |
| *C07C 37/16* | (2006.01) |
| *C07C 39/23* | (2006.01) |
| *C07C 41/06* | (2006.01) |
| *C07D 215/06* | (2006.01) |
| *C07D 215/14* | (2006.01) |
| *C07D 215/20* | (2006.01) |
| *C07D 215/48* | (2006.01) |
| *C07D 311/58* | (2006.01) |
| *C07D 311/64* | (2006.01) |

(52) U.S. Cl.
CPC ............ *A61K 31/353* (2013.01); *A61K 45/06* (2013.01); *A61P 25/08* (2018.01); *C07C 37/16* (2013.01); *C07C 39/23* (2013.01); *C07C 41/06* (2013.01); *C07D 215/06* (2013.01); *C07D 215/14* (2013.01); *C07D 215/20* (2013.01); *C07D 215/48* (2013.01); *C07D 311/58* (2013.01); *C07D 311/64* (2013.01)

(58) Field of Classification Search
USPC ........................................................ 514/312
See application file for complete search history.

(56) References Cited

U.S. PATENT DOCUMENTS

| | | | |
|---|---|---|---|
| 9,017,737 B2 | 4/2015 | Kikuchi et al. |
| 9,125,859 B2 | 9/2015 | Whalley et al. |
| 9,474,726 B2 | 10/2016 | Guy et al. |
| 9,675,654 B2 | 6/2017 | Parolaro et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 | 8/2020 | Whalley et al. |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 | 5/2021 | Liu et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 | 5/2022 | Whalley et al. |
| 11,357,741 B2 | 6/2022 | Guy et al. |
| 11,400,055 B2 | 8/2022 | Guy et al. |
| 11,406,623 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy et al. |
| 12,023,305 B2 | 7/2024 | Whalley et al. |
| 12,064,398 B2 | 8/2024 | Wright et al. |
| 12,064,399 B2 | 8/2024 | Guy et al. |
| 2015/0274623 A1 | 10/2015 | Makriyannis et al. |
| 2015/0359756 A1 | 12/2015 | Guy et al. |
| 2017/0008868 A1 | 1/2017 | Dialer et al. |
| 2017/0239193 A1 | 8/2017 | Guy et al. |
| 2018/0071210 A1 | 3/2018 | Wilkhu et al. |
| 2018/0228751 A1 | 8/2018 | Stott et al. |
| 2019/0167583 A1 | 6/2019 | Shah |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |

(56) References Cited

U.S. PATENT DOCUMENTS

| | | |
|---|---|---|
| 2022/0288055 A1 | 9/2022 | Silcock et al. |
| 2022/0362149 A1 | 11/2022 | Shah |
| 2022/0378714 A1 | 12/2022 | Guy et al. |
| 2022/0378715 A1 | 12/2022 | Guy et al. |
| 2022/0378738 A1 | 12/2022 | Guy et al. |
| 2022/0387347 A1 | 12/2022 | Whalley et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 3/2024 | Guy et al. |
| 2024/0130981 A1 | 4/2024 | Wilkhu et al. |
| 2024/0131041 A1 | 4/2024 | Tse et al. |
| 2024/0165048 A1 | 5/2024 | Guy et al. |
| 2024/0207220 A1 | 6/2024 | Guy et al. |
| 2024/0215910 A1 | 7/2024 | Tse et al. |
| 2024/0226032 A9 | 7/2024 | Wilkhu et al. |
| 2024/0226123 A9 | 7/2024 | Tse et al. |
| 2024/0238218 A1 | 7/2024 | Silcock et al. |
| 2024/0254066 A1 | 8/2024 | Silcock et al. |
| 2024/0254072 A1 | 8/2024 | Silcock et al. |

FOREIGN PATENT DOCUMENTS

| | | |
|---|---|---|
| WO | WO 2014/062965 A1 | 4/2014 |
| WO | WO 2015/193667 A1 | 12/2015 |
| WO | WO 2015/193668 A1 | 12/2015 |
| WO | WO 2016/094810 A2 | 6/2016 |
| WO | WO 2016/135308 A1 | 9/2016 |
| WO | WO 2016/203239 A1 | 12/2016 |
| WO | WO 2018/061007 A1 | 4/2018 |
| WO | WO 2018/205022 A1 | 11/2018 |

OTHER PUBLICATIONS

Carral-Menoyo A, Misol A, Gómez-Redondo M, Sotomayor N, Lete E. Palladium (II)-Catalyzed Intramolecular C—H Alkenylation for the Synthesis of Chromanes. The Journal of Organic Chemistry. Jan. 14, 2019;84(4):2048-60. (Year: 2019).*

Schafroth MA, Rummelt SM, Sarlah D, Carreira EM. Enantioselective Iridium-catalyzed allylic cyclizations. Organic letters. Jun. 16, 2017;19(12):3235-8. (Year: 2017).*

Huffman JW, Yu S. Synthesis of a tetracyclic, conformationally constrained analogue of Δ8-THC. Bioorganic & medicinal chemistry. Dec. 1, 1998;6(12):2281-8. (Year: 1998).*

Friedman D, Devinsky O. Cannabinoids in the treatment of epilepsy. New England Journal of Medicine. Sep. 10, 2015;373(11):1048-58. (Year: 2015).*

Kimball, A. W. et al., "Chemical Protection against Ionizing Radiation," Radiation Research, 7:1-12 (1957).

Litchfield, J. T. & Wilcoxon, F., "A simplified method of evaluating dose-effect experiments," Fed Proc. Mar. 1948; 7(1 Pt 1):240, 15 pages.

Loscher, W. et al., "The role of technical, biological and pharmacological factors in the laboratory evaluation of anticonvulsant drugs. II. Maximal electroshock seizure models," Epilepsy Res. Mar. 1991; 8(2):79-94. doi: 10.1016/0920-1211(91)90075-q.

Epidiolex® (cannabidiol) oral solution, CV, Prescribing Information, 2018, 30 pages; https://www.accessdata.fda.gov/drugsatfda_docs/label/2018/210365lbl.pdf.

Harvey, D. J., "Characterization of the butyl homologues of Δ1-tetrahydrocannabinol, cannabinol and cannabidiol in samples of cannabis by combined gas chromatography and mass spectrometry," J. Pharm. Pharmac., 28:280-285 (1976).

Hill, T. D. M. et al., "Cannabidivarin-rich cannabis extracts are anticonvulsant in mouse and rat via a CB1 receptor-independent mechanism," British Journal of Pharmacology, 170:679-692 (2013).

Morales, P. et al., "An Overview on Medicinal Chemistry of Synthetic and Natural Derivatives of Cannabidiol," Frontiers in Pharmacology, 8:422 (2017); doi:10.3389/fphar.2017.00422, 18 pages.

Pertwee, "The Pharmacology and Therapeutic Potential of Cannabidiol," Cannabinoids, Chapter 3, DiMarzo, V. (Ed.), pp. 32-83 (2004).

Vree et al., "Identification of hashish of tetrahydrocannabinol, cannabidiol and cannabinol analogues with a methyl side-chain," J. Pharm. Pharmac. 24:7-12 (1972).

U.S. Appl. No. 15/640,033, filed Jun. 30, 2017.
U.S. Appl. No. 16/467,639, filed Jun. 7, 2019.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 17/050,956, filed Oct. 27, 2020.
U.S. Appl. No. 16/935,005, filed Jul. 21, 2020.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/680,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.

(56) References Cited

OTHER PUBLICATIONS

U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/786,949, filed Jun. 17, 2022.
U.S. Appl. No. 17/853,367, filed Jun. 29, 2022.
U.S. Appl. No. 17/816,349, filed Jul. 29, 2022.
U.S. Appl. No. 17/819,046, filed Aug. 11, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18,006,133, filed Jan. 19, 2023.
U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.

* cited by examiner

Figure 1. Effect of Compound 12a on the electroshock-induced generalised seizure threshold (MEST) in the mouse
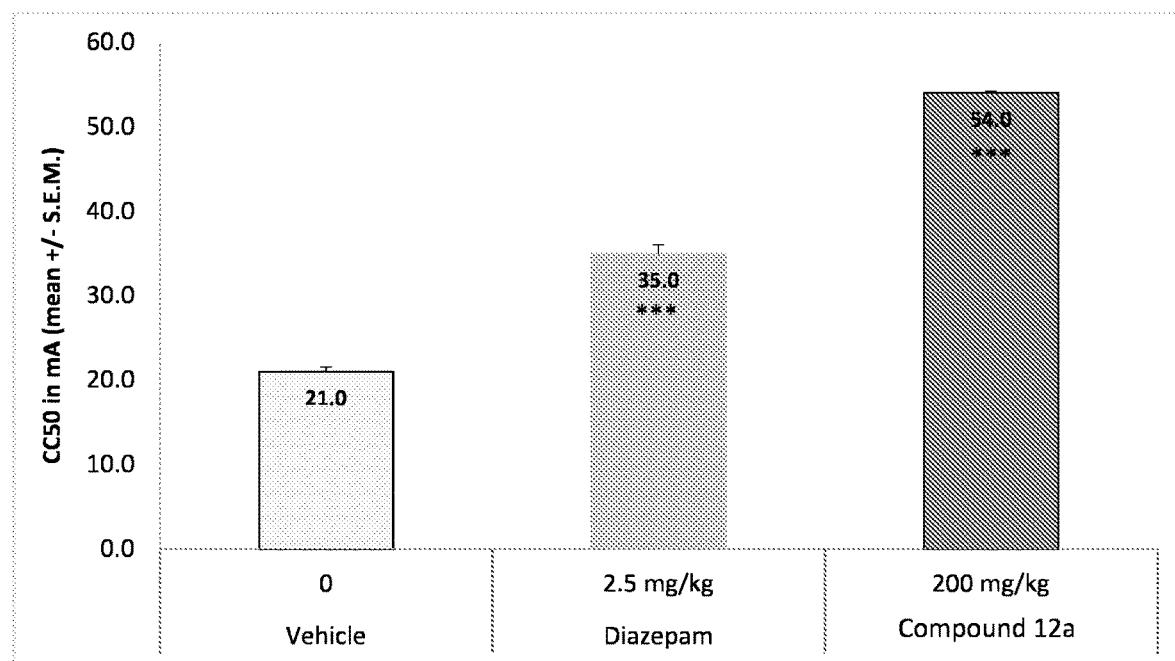

Figure 2. Effect of Compound 12b on the electroshock-induced generalised seizure threshold (MEST) in the mouse
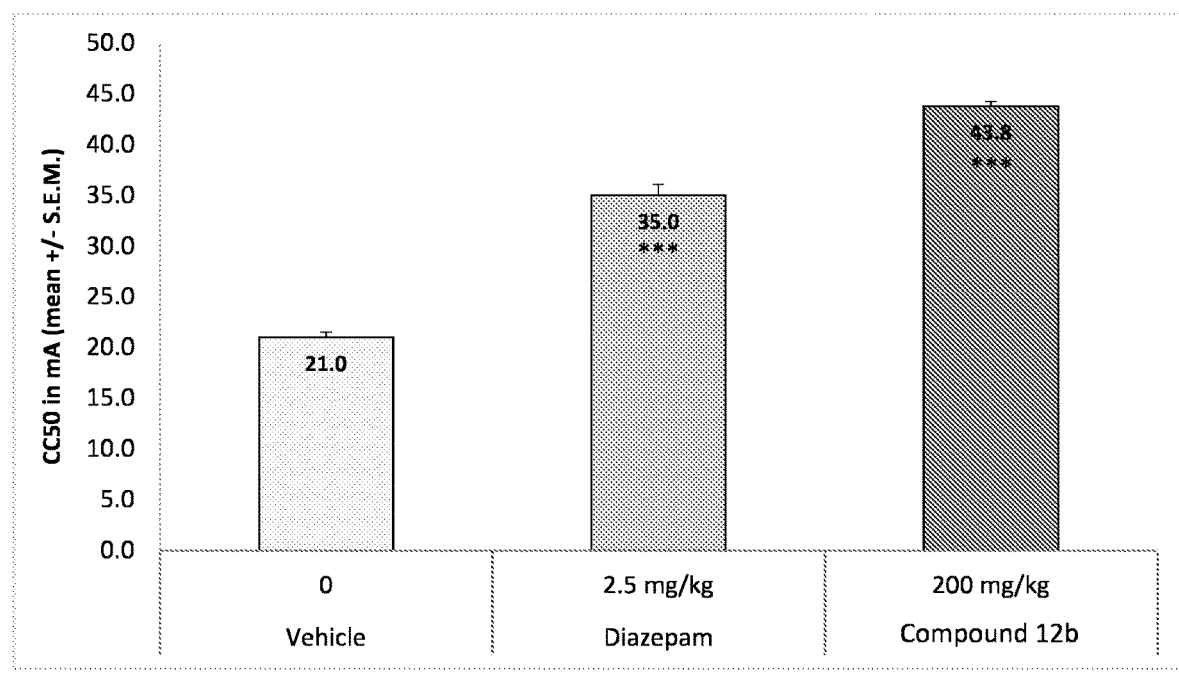

Figure 3. Effect of Compound 18a on the electroshock-induced generalised seizure threshold (MEST) in the mouse
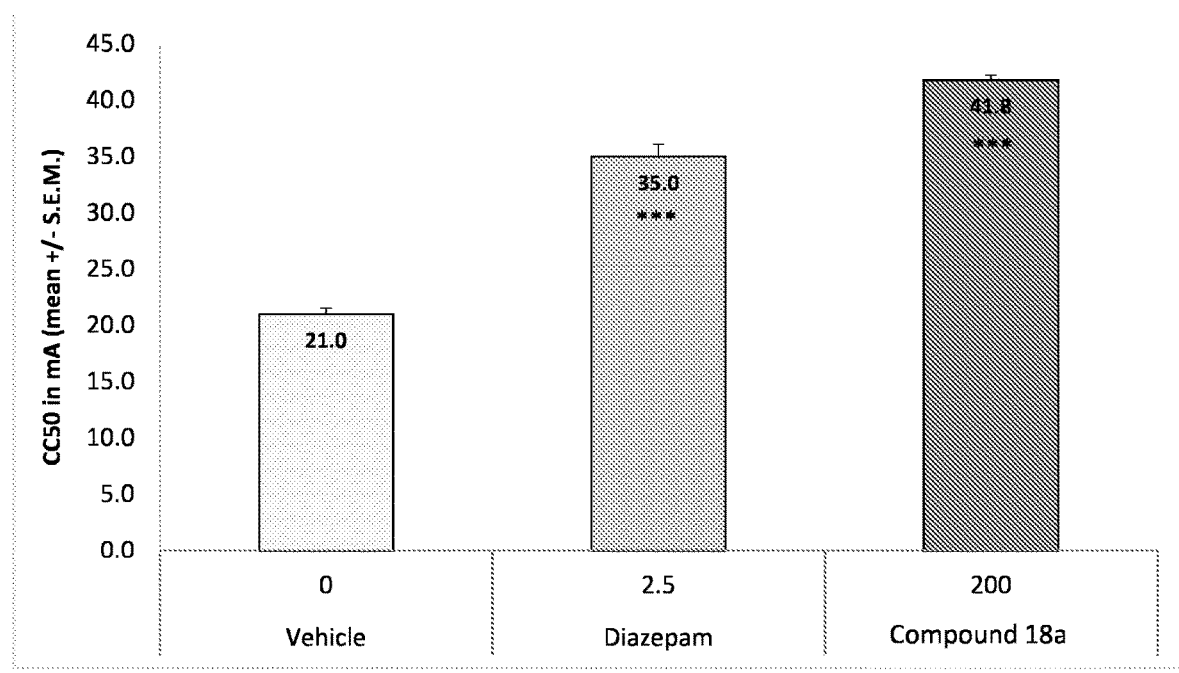

Figure 4. Effect of Compound 18b on the electroshock-induced generalised seizure threshold (MEST) in the mouse
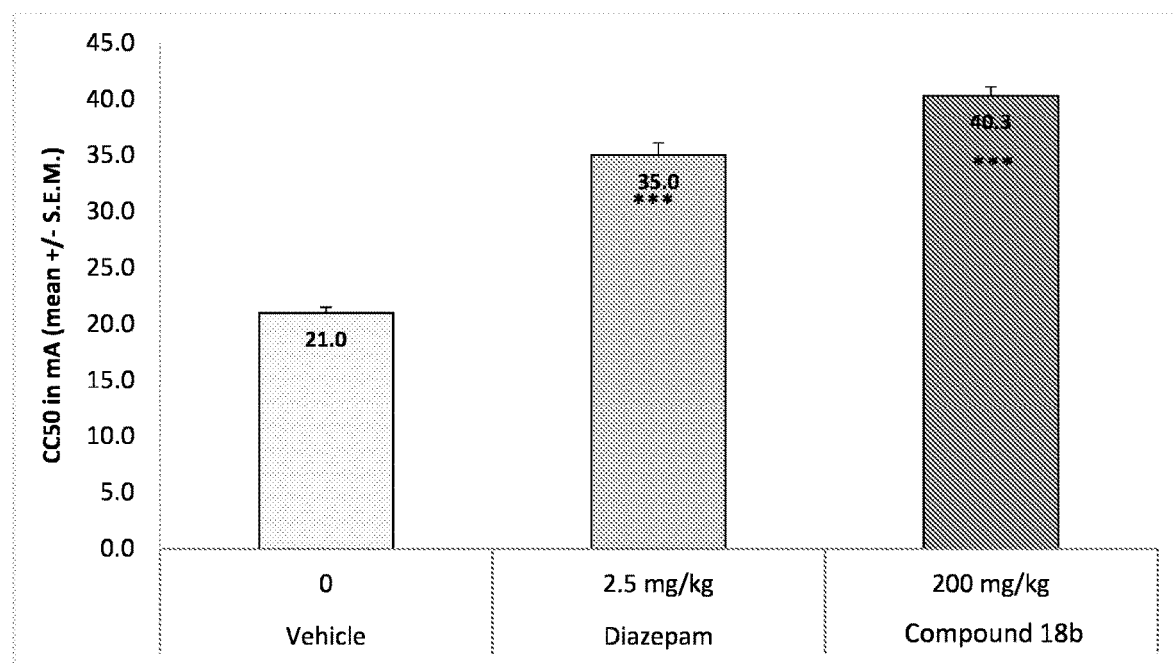

CANNABINOID DERIVATIVES AS PHARMACEUTICALLY ACTIVE COMPOUNDS AND METHODS OF PREPARATION THEREOF

CROSS-REFERENCE TO RELATED APPLICATIONS

This application claims the benefit of International PCT Application No. PCT/GB2020/051723, filed Jul. 17, 2020; and Great Britain Application No. 1910389.4, filed Jul. 19, 2019; each of the aforementioned applications are incorporated herein by reference in its entirety.

FIELD OF THE INVENTION

The present invention relates to a group of cannabinoid derivatives as pharmaceutically active compounds and methods of preparation thereof.

The cannabinoid derivatives of the invention are analogues of cannabidiol (CBD). CBD is a non-psychoactive cannabinoid which has been used to treat various diseases and disorders. While such treatments hold promise, there remains a need in the art for more effective treatments and this has been brought about by way of the cannabinoid derivatives of the invention.

BACKGROUND TO THE INVENTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. Cannabis is a genus of flowering plants in the family *Cannabaceae,* comprising the species *Cannabis sativa, Cannabis indica,* and *Cannabis ruderalis* (sometimes considered as part of *Cannabis sativa*).

Cannabis plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPRS. The principle cannabinoids present in cannabis plants are cannabinoid acids Δ9-tetrahydrocannabinolic acid (Δ9-THCA) and cannabidiolic acid (CBDA) with small amounts of their respective neutral (decarboxylated) cannabinoids. In addition, cannabis may contain lower levels of other minor cannabinoids.

There are currently four cannabinoid-based pharmaceutical approved products on the market. These are: dronabinol (Marinol®) which is a synthetic tetrahydrocannabinol (THC) approved for the treatment of loss of appetite in AIDS and the treatment of severe nausea and vomiting caused by cancer chemotherapy; nabilone (Cesamet®) which is a synthetic cannabinoid and an analog of THC which is approved for the treatment of nausea and vomiting caused by cytotoxic chemotherapy unresponsive to conventional antiemetics; nabiximols (Sativex®) a mixture of two cannabis plant extracts approved for the treatment of neuropathic pain, spasticity, overactive bladder, and other symptoms of multiple sclerosis; and highly purified botanical CBD (Epidiolex®) approved in the United States for the treatment of Dravet syndrome and Lennox-Gastaut syndrome in children and adults over the age of 2 years.

As can be seen above cannabinoids are a class of compounds which may be derived naturally from the cannabis plant or produced semi-synthetically or synthetically via chemical synthesis.

More than 100 different cannabinoids have been identified. These cannabinoids can be split into different groups as follows: phytocannabinoids; endocannabinoids and synthetic cannabinoids (which may be novel cannabinoids or synthetically produced versions of phytocannabinoids or endocannabinoids). The Handbook of Cannabis, Roger Pertwee, Chapter 1, pages 3 to 15 details the cannabinoids known to date.

Cannabidiol (CBD) is a major cannabinoid constituent of Cannabis species, such as the hemp plant (*Cannabis sativa*). Unlike other cannabinoids, such as THC, cannabidiol does not bind to CB1 or CB2 receptors, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

The synthetic production of the metabolite of CBD, 7-hydroxy-cannabidiol, (7-OH CBD) is disclosed in WO 01/95899. The compound was tested in a model of inflammation and found to be effective. The application goes on to suggest that the compound may be of use as an analgesic, anti-anxiety, anti-convulsant, neuroprotective, anti-psychotic and anti-inflammatory based on the mechanisms the compound displays in the model of inflammation.

The present invention relates to novel cannabinoid compounds which are biologically active and hence useful in the treatment of diseases. Such novel compounds may be administered by a wide variety of routes including but not limited to oral, transdermal, buccal, nasal, pulmonary, rectal or ocular. Such compounds may be used for the treatment or prevention of a medical condition such as epilepsy, pain, inflammation and cancer.

BRIEF SUMMARY OF THE DISCLOSURE

In accordance with a first aspect of the present invention there is provided a compound of general Formula I or a salt thereof,

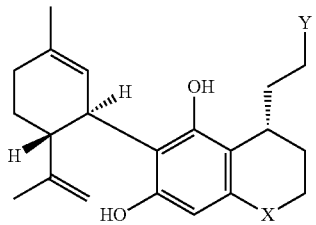

Formula I where X is either $CH_2$; O; NBoc; NFMoc; NZ; NTs; NAc; NC(O)iPr; NBz or NH and Y is either H or OH.

In accordance with a second aspect of the present invention there is provided a compound of general Formula II or a salt thereof,

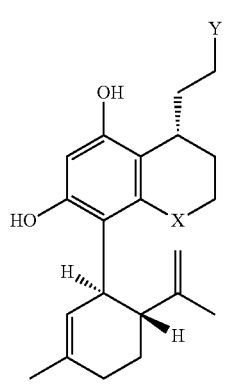

Formula II where X is either $CH_2$; O; NBoc; NFMoc; NZ; NTs; NAc; NC(O)iPr; NBz or NH and Y is either H or OH.

In accordance with a third aspect of the present invention there is provided a pharmaceutical composition comprising the compound of general Formula I or Formula II.

Preferably the pharmaceutical composition is selected from a tablet, a capsule, a granule, an oral solution, a powder for inhalation, a sprinkle, an oral solution and a suspension.

Preferably the pharmaceutical composition comprises one or more of: an excipient selected among a carrier, an oil, a disintegrant, a lubricant, a stabilizer, a flavouring agent, an antioxidant, a diluent and another pharmaceutically effective compound.

In accordance with a fourth aspect of the present invention there is provided a compound of general Formula I or Formula II for use as a medicament.

In accordance with a fifth aspect of the present invention there is provided a compound of general Formula I or Formula II for use in the treatment of epilepsy.

In accordance with a sixth aspect of the present invention there is provided a comprising administering a pharmaceutical preparation comprising a compound of general Formula I or Formula II.

In accordance with a seventh aspect of the present invention there is provided a process for the production of a compound of general Formula I or Formula II comprising reacting a resorcinol unit of Structure 1a-j via a Friedel-Crafts 1,4-addition to produce compounds of Structures 2a to 2j or 3a to 3j followed by subsequent steps to produce the compounds of general Formula I or Formula II via intermediates.

In accordance with an eighth aspect of the present invention there is provided an intermediate formed in the process of the production of a compound of general Formula I or Formula II.

DEFINITIONS

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds that are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

DETAILED DESCRIPTION OF THE INVENTION

The following describes the production of the novel cannabinoid derivatives as claimed in the present invention. The structure and absolute configuration of the compounds produced were determined by X-ray crystallographic analysis, using a molybdenum X-Ray source.

Example 1: Method of Manufacture of Normal CBD Derivatives

This example describes a novel method of synthesis which was used to produce novel analogues of normal CBD which demonstrated pharmacological activity. Scheme 1 below describes the initial reaction which was used to produce the primary intermediate and Scheme 2 describes the production of the normal CBD derivatives which were formed via a number of intermediates.

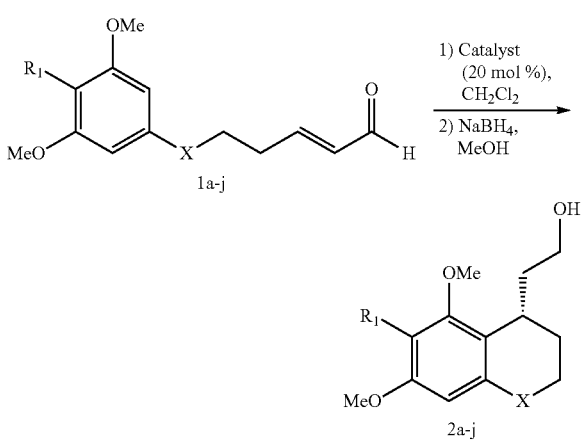

Scheme 1 Friedel-Crafts 1,4-addition reaction

Where $R_1$=H or OMe and X=$CH_2$; O; NBoc; NFMoc; NZ; NTs; NAc; NC(O)iPr; NBz or NH The resorcinol unit, in Structures 1a to 1j (shown below), underwent a Friedel-Crafts 1,4-addition reaction as shown in Scheme 1 to produce compounds of Structures 2a to 2j described below.

Various catalysts were tested. Silylated Jorgensen-Hayashi type gave poor yields but excellent selectivity. MacMillan-type catalysts gave better yields but poorer enantioselectivities.
Structures 1a-j
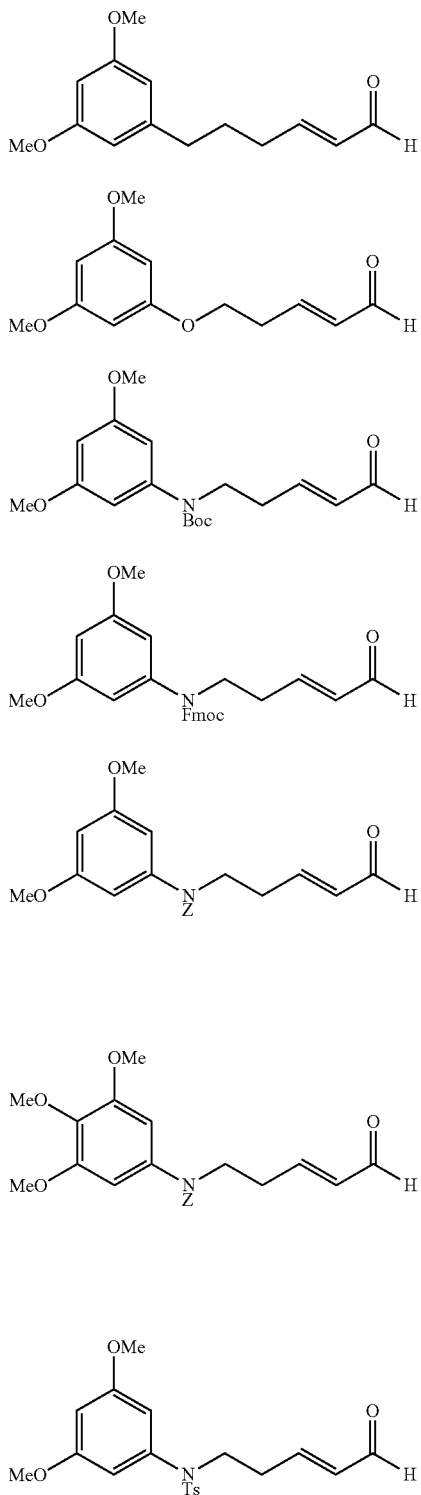
-continued
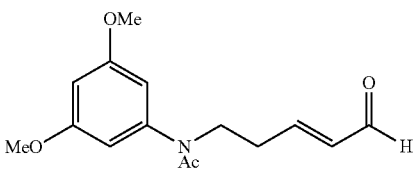
1h
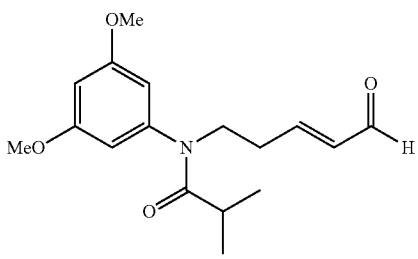
1i
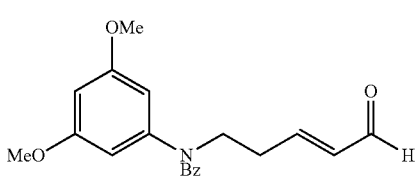
1j
Structures 2a-j
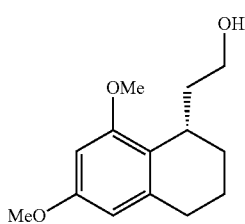
2a
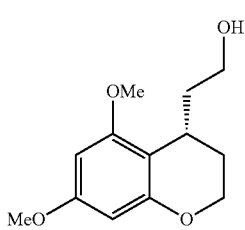
2b
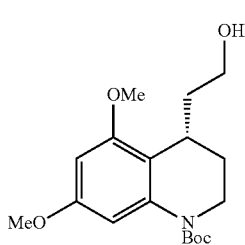
2c
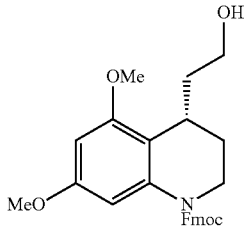
2d 2e 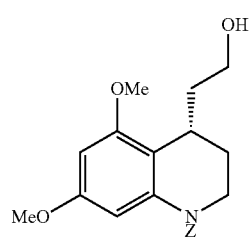
2f 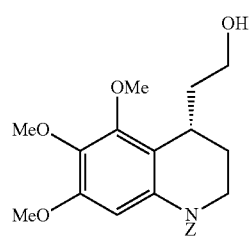
2g 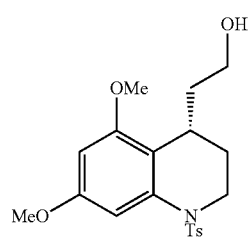
2h 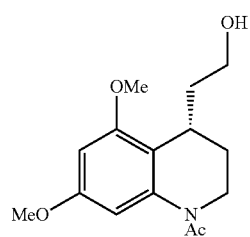
2i 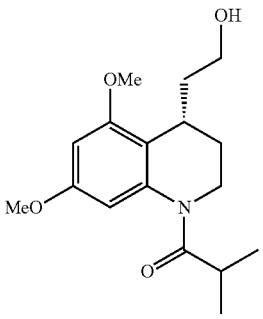
2j 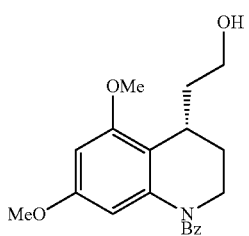
Structures 3a-j
3a 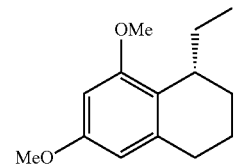
3b 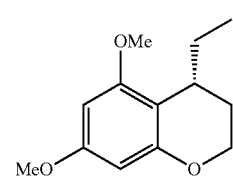
3c 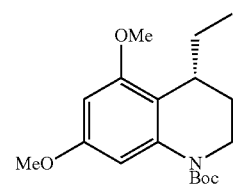
3d 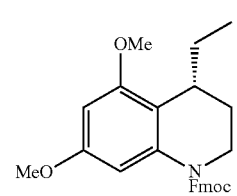
3e 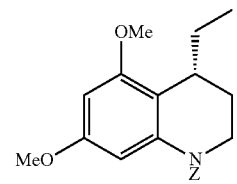

3f
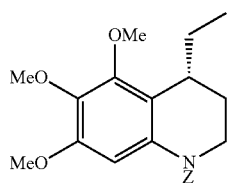
3g
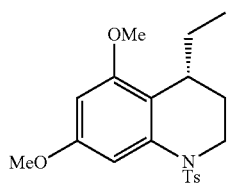
3h
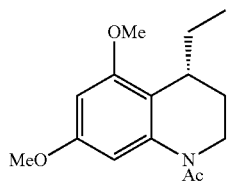
3i
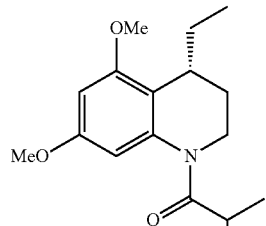
3j
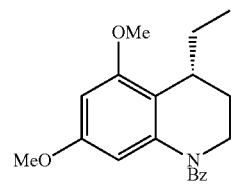
The compound of Structures 2a to 2j or 3a to 3j (shown above) were then reacted as shown in Scheme 2 below to derive two different normal CBD derivatives 11a to 11j or 12a to 12j.
Deprotection of the derivatives 11c-j and 12 c-j further produced compounds 13 and 14.
Scheme 2 Synthesis of normal CBD analogues
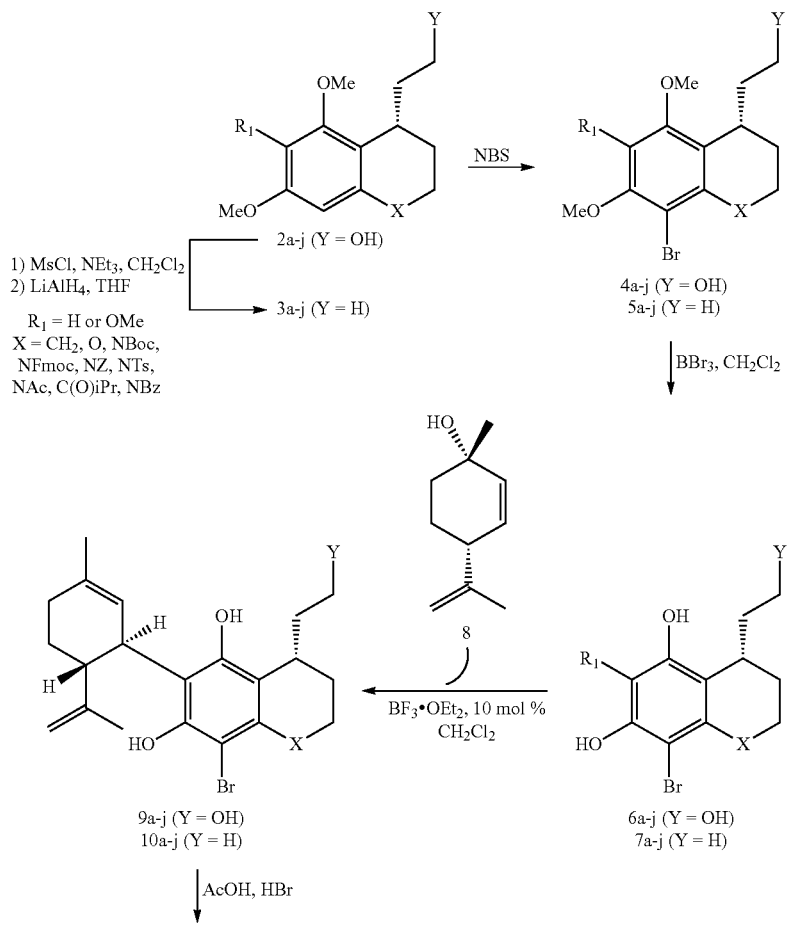

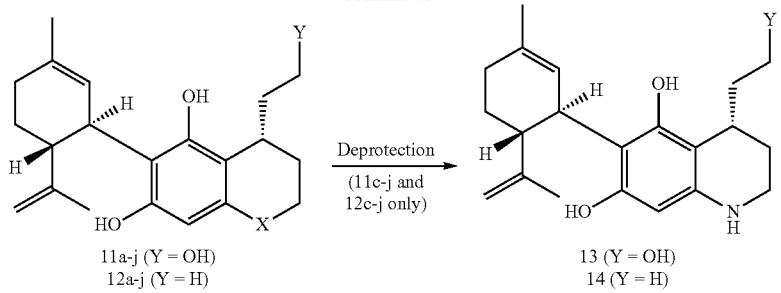
11a-j (Y = OH)
12a-j (Y = H)
NBS: N-bromosuccinimide
Deprotection
(11c-j and 12c-j only)
13 (Y = OH)
14 (Y = H)
Synthesis of Intermediates 4a to 4j or 5a to 5j
Intermediates 2a-2j or 3a-3j were brominated with N-bromosuccinimide (NBS) to create arylbromide system compounds 4a-4j or 5a-5j shown below.
Structures 4a-4j
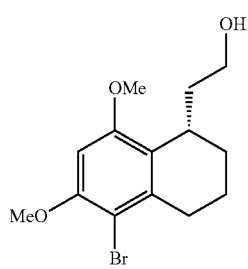
4a
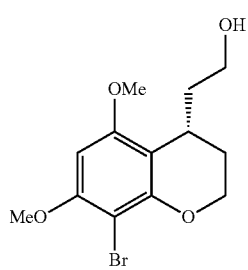
4b
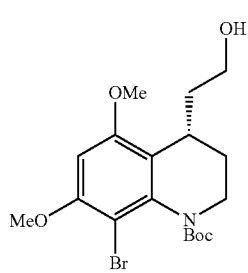
4c
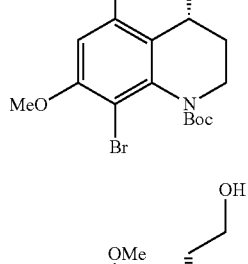
4d
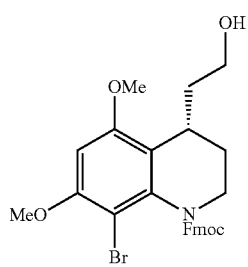
4e
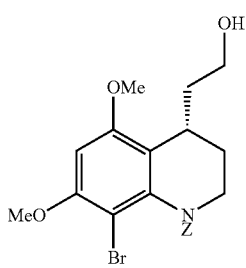
4f
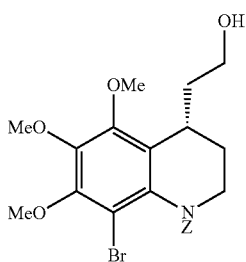
4g
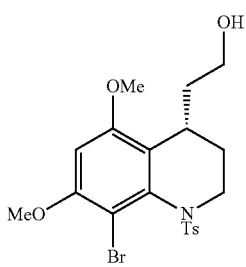
4h
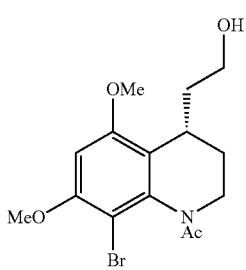

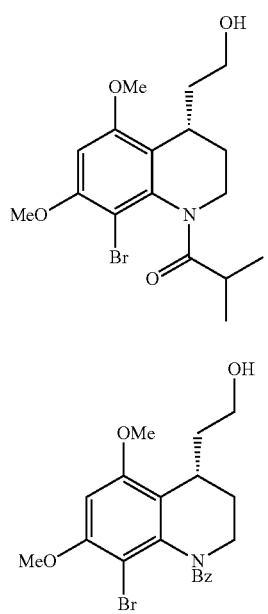
4i
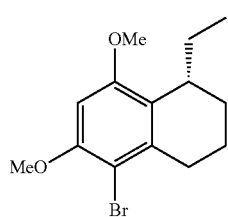
4j
Structures 5a-5j
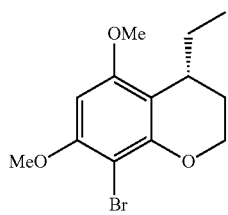
5a
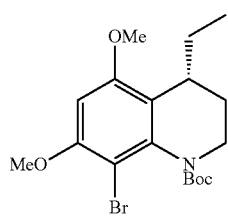
5b
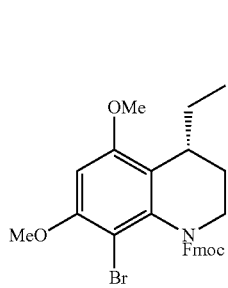
5c
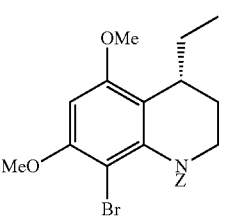
5e
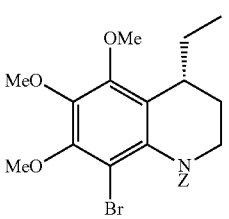
5f
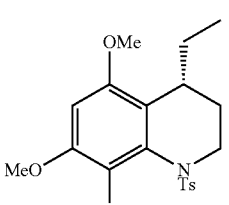
5g
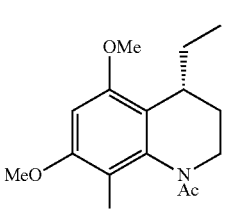
5h
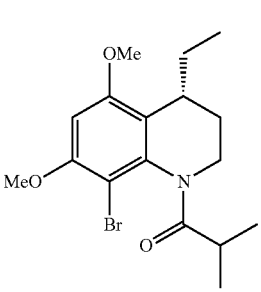
5i
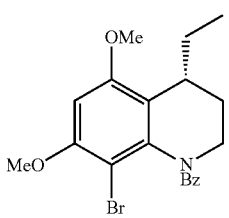
5j
Synthesis of Intermediates 6a to 6j or 7a to 7j
Intermediates 4a-4j or 5a-5j were O-demethylated with boron tribromide in the presence of dichloromethane which resulted in the deprotected chiral resorcinol compounds as described in 6a to 6j or 7a to 7j depicted below.

Structures 6a-6j
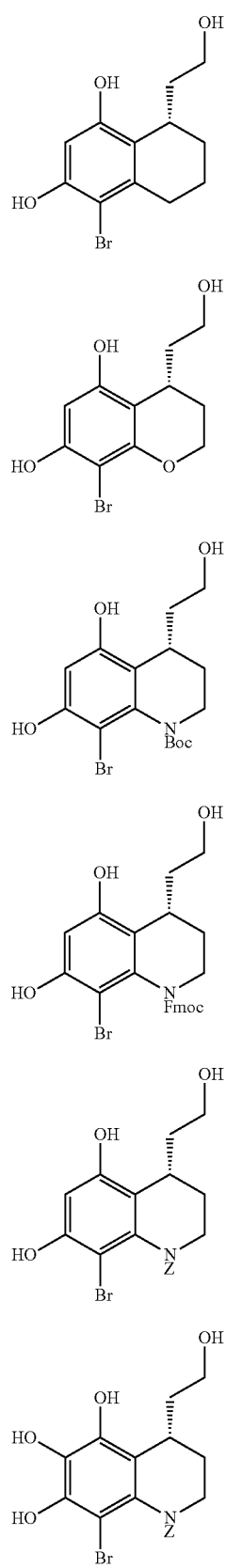
6a
6b
6c
6d
6e
6f
Structures 7a-7j
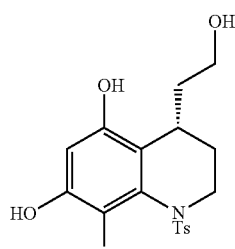 6g
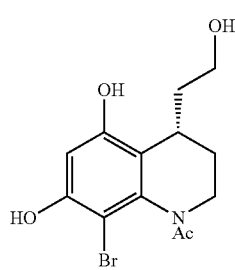 6h
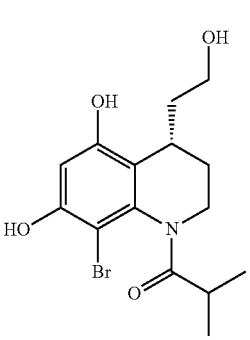 6i
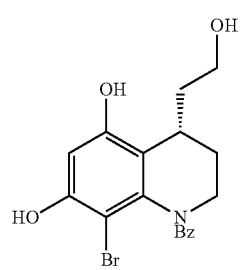 6j
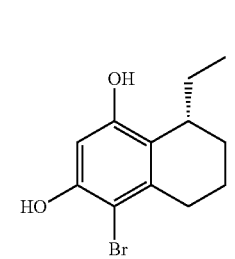 7a
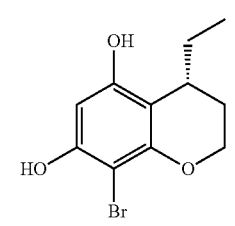 7b

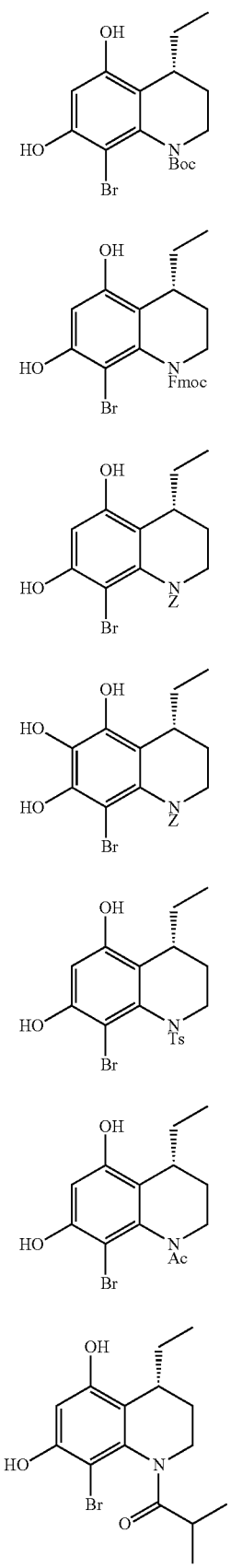

7c

7d

7e

7f

7g

7h

7i

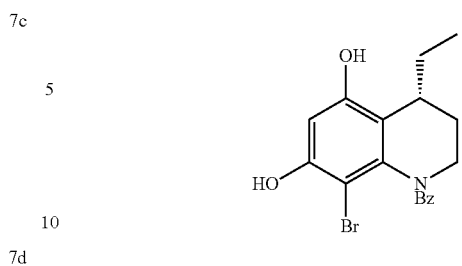

7j

Synthesis of Intermediates 9a to 9j (except 9f) or 10a to 10j (except 10f)

Coupling of the brominated intermediates of 6a-6j or 7a-7j with menthadienol (shown as structure 8 in Scheme 2) in the presence of boron trifluoride diethyl etherate produced the intermediates 9a to 9j (except 9f which is not possible) or 10a to 10j (except 10f which is not possible). These structures are depicted below.

Structures 9a-j (note 9f is not possible)

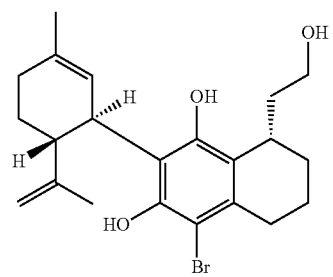

9a

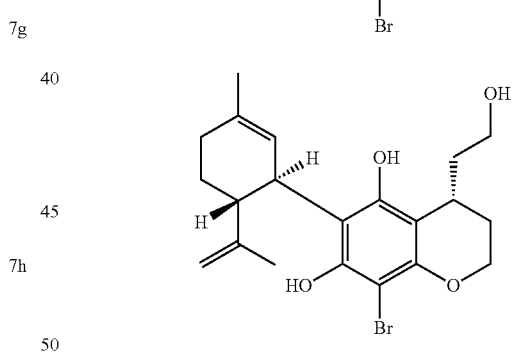

9b

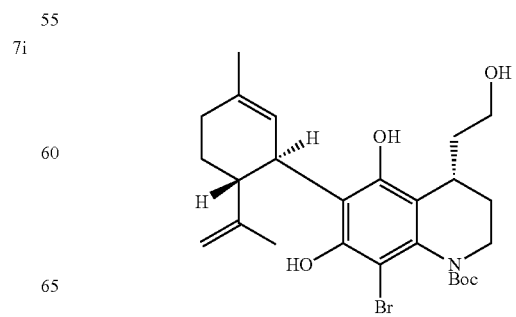

9c

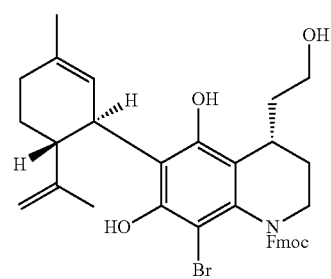
9d
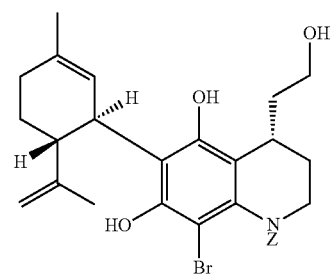
9e
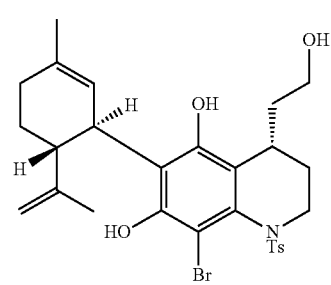
9g
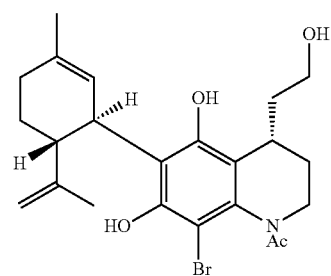
9h
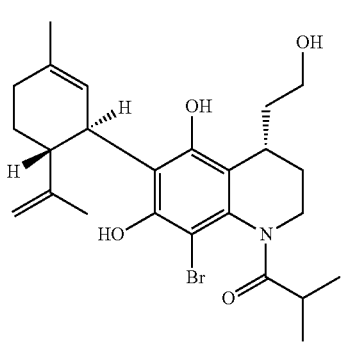
9i
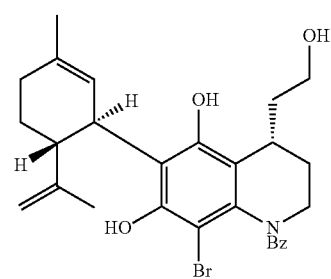
9j
Structures 10a-j (note 10f is not possible)
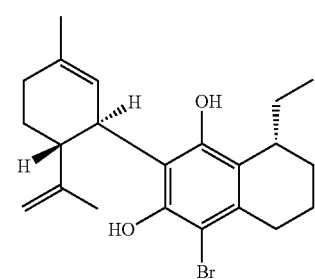
10a
10b
10c
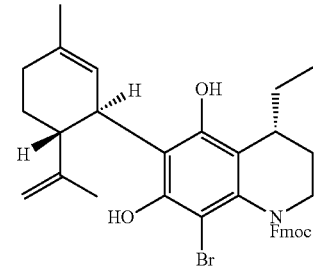
10d

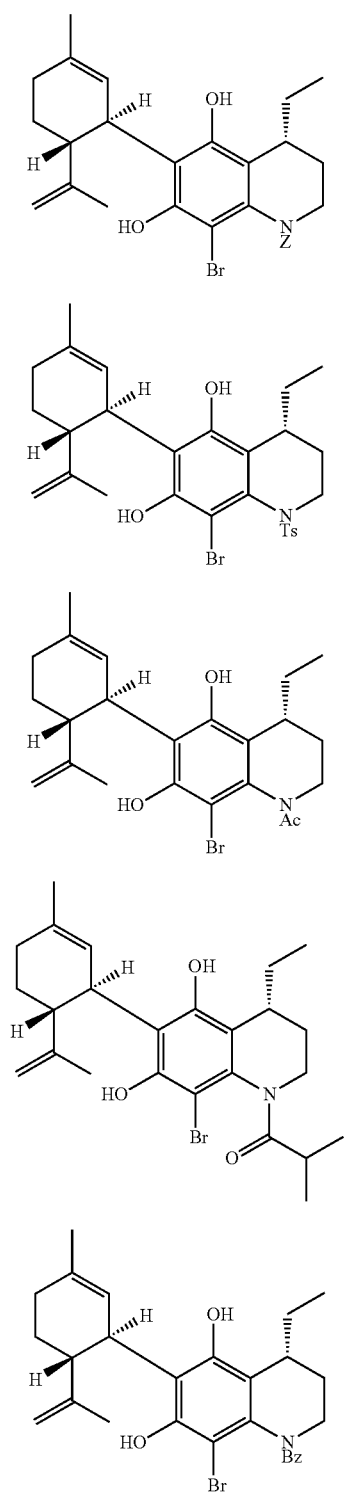
Structures 11a-j (note 11f is not possible)
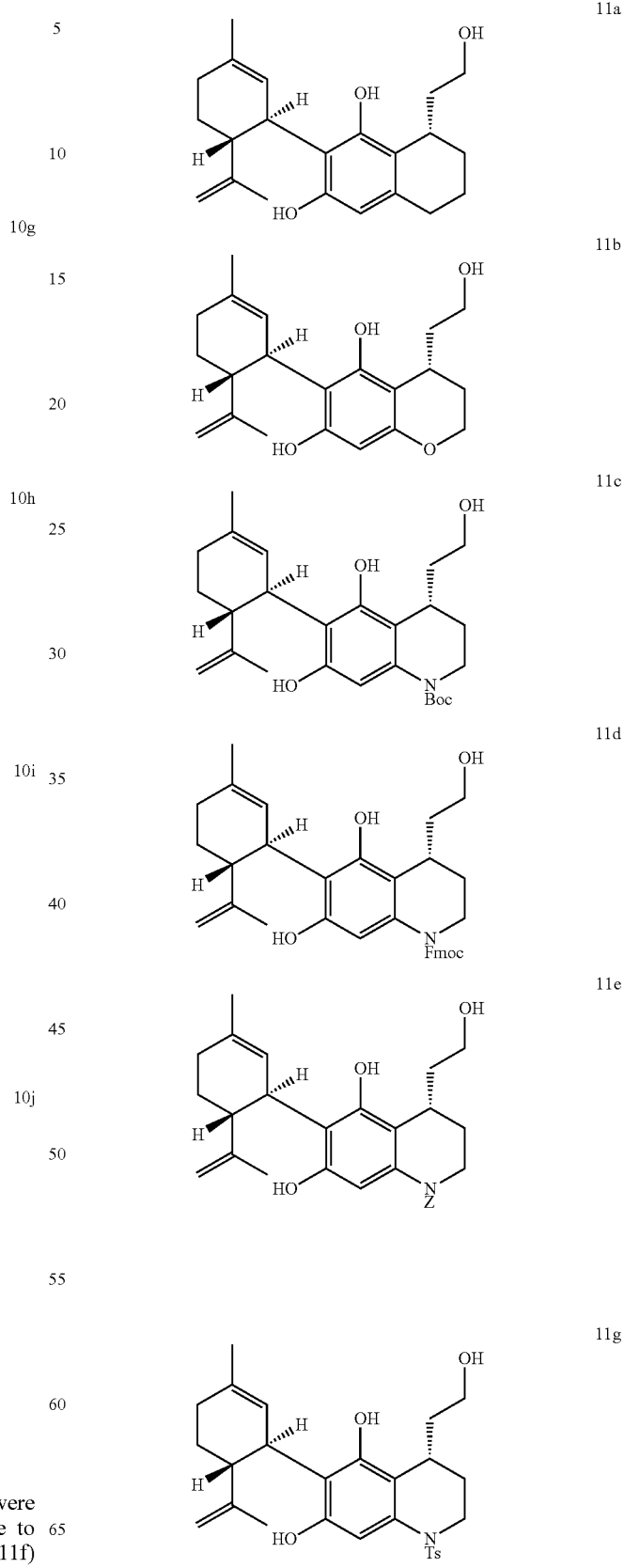
Synthesis of Normal CBD Derivatives 11a to 11j
(Except 11f) or 12a to 12j (except 12f)
9a to 9j (except 9f) or 10a to 10j (except 10f) were debrominated with acetic acid and hydrogen bromide to produce the normal CBD derivatives 11a to 11j (except 11f) or 12a to 12j (except 12f) shown below.

23
-continued
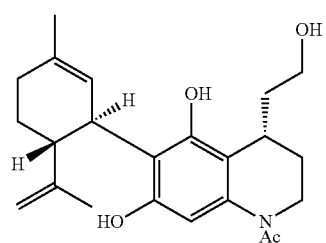
11h
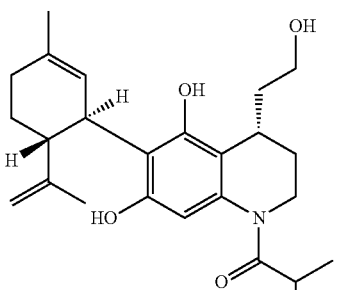
11i
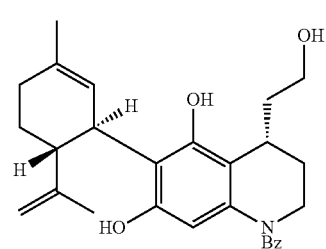
11j
Structures 12a-j (note 12f is not possible)
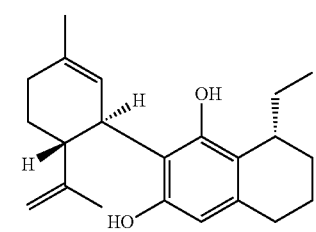
12a
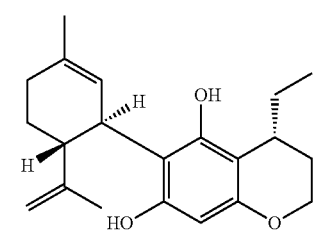
12b
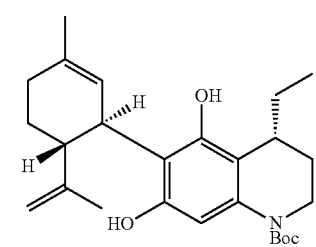
12c
24
-continued
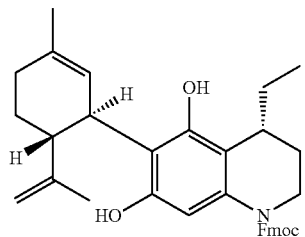
12d
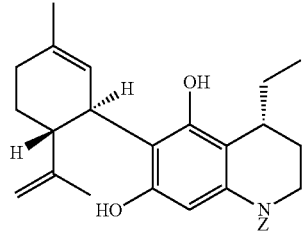
12e
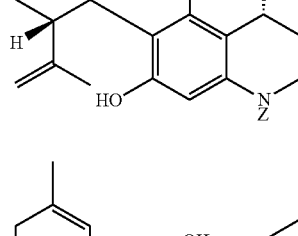
12g
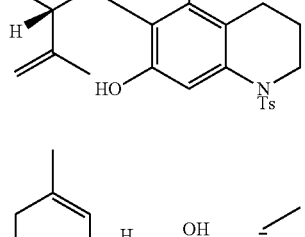
12h
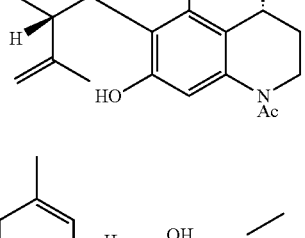
12i
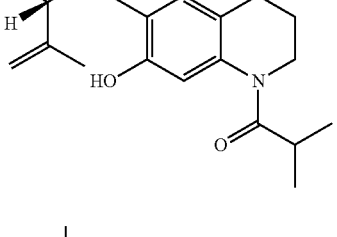
12j Furthermore, the N-protected moieties compounds 11c-11j (except 11f) and 12c to 12j (except 12f) can be deprotected to give the two NH derivatives, compounds 13 and 14, shown below.

Structures 13 and 14

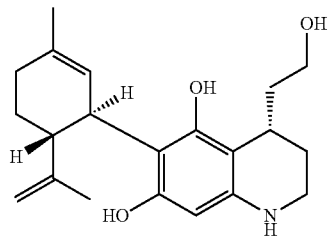

13

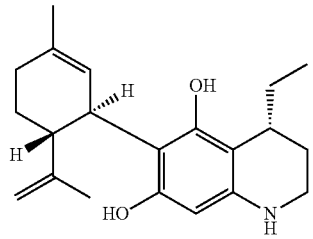

14

Example 2: Method of Manufacture of Abnormal CBD Derivatives

This example describes a novel method of synthesis which was used to produce novel analogues of abnormal CBD which demonstrated pharmacological activity. Scheme 1 depicted in Example 1 describes the initial reaction which was used to produce the primary intermediates 2a to 2j and 3a to 3j and Scheme 3 describes the production of the abnormal CBD derivatives which were formed via a number of intermediates.

Scheme 3 Synthesis of abnormal CBD analogues

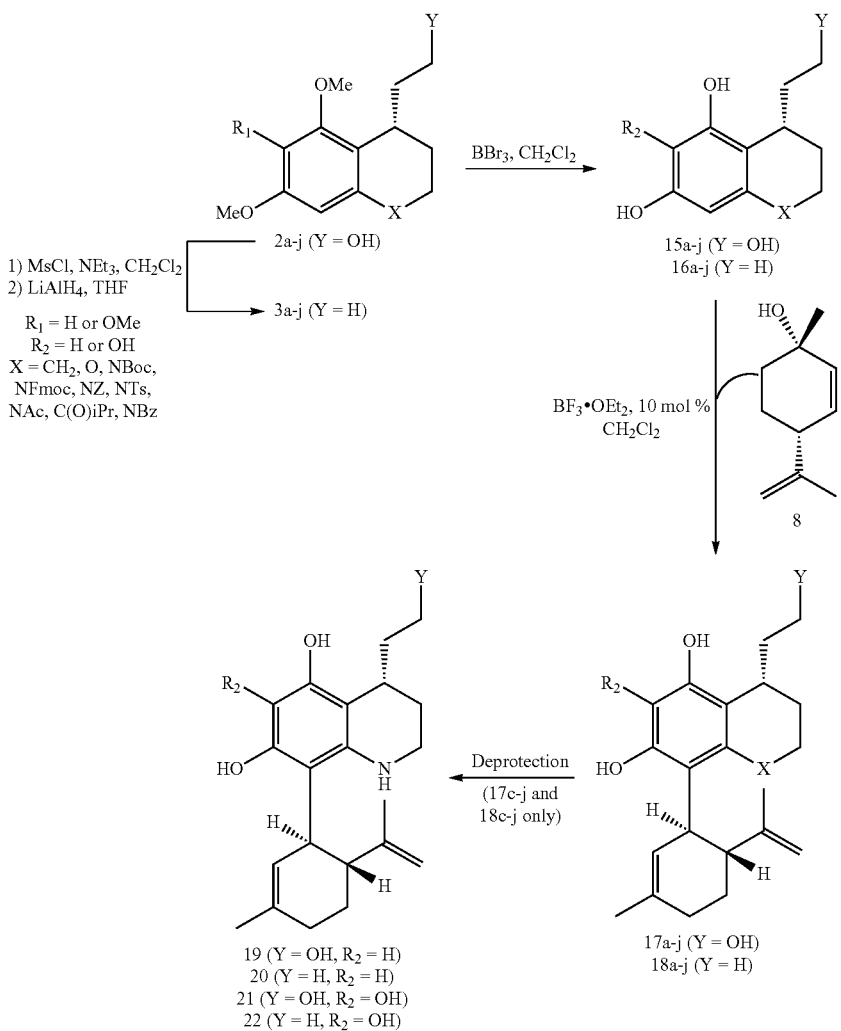

Synthesis of Intermediates 15a to 15j or 16a to 16j
Intermediates 2a to 2j or 3a to 3j were O-demethylated with boron tribromide in the presence of dichloromethane which resulted in the deprotected chiral resorcinol compounds as described in 15a to 15j or 16a to 16j below.
Structures 15a-j
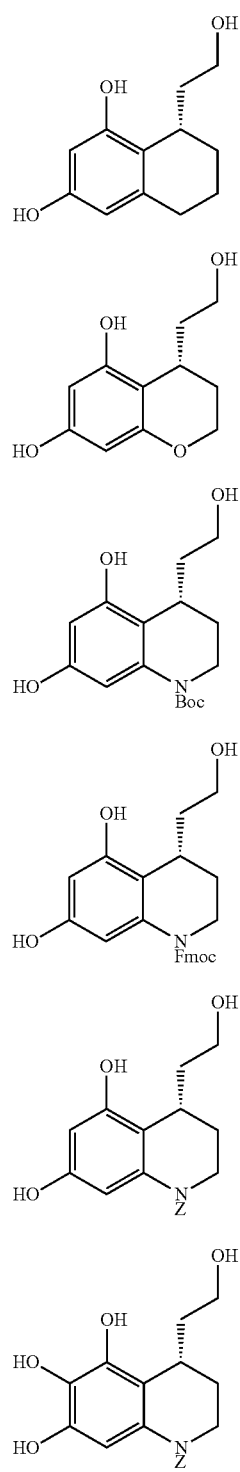
Structures 16a-j
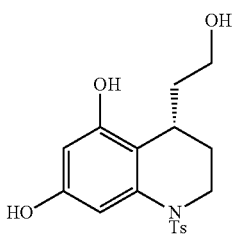
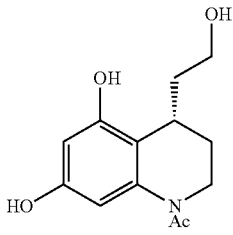
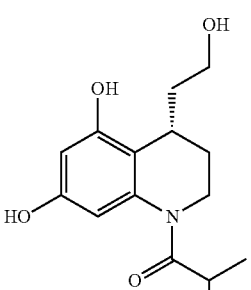
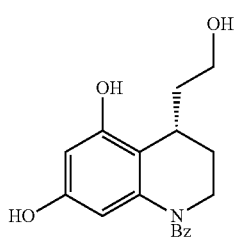
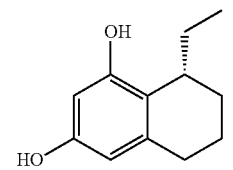
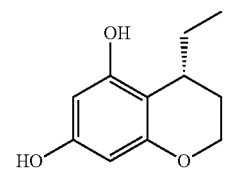
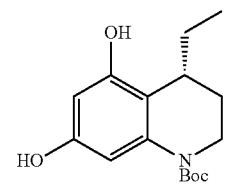

-continued
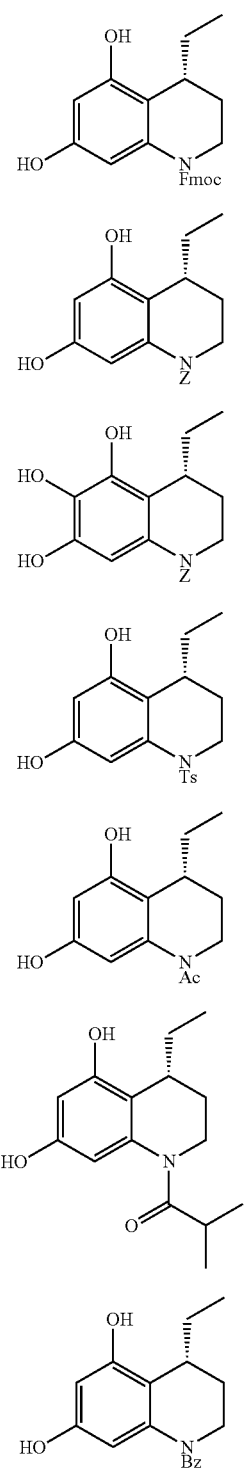
16d
16e
16f
16g
16h
16i
16j
Synthesis of Abnormal CBD Derivatives 17a to 17j or 18a to 18j
Coupling of the intermediates of 15a-15j or 16a-16j with menthadienol (shown as structure 8 in Scheme 3) in the presence of boron trifluoride diethyl etherate produced the abnormal CBD derivatives 17a to 17j or 18a to 18j depicted below.
Structures 17a-17j
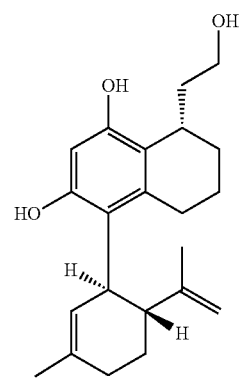
17a
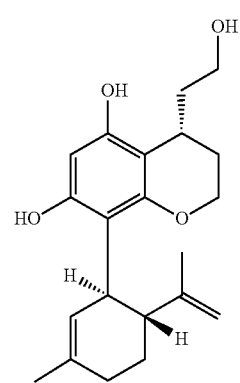
17b
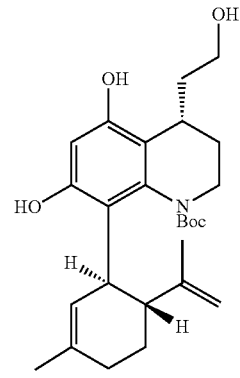
17c
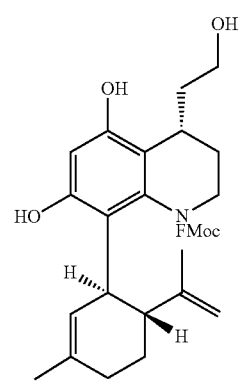
17d 17e
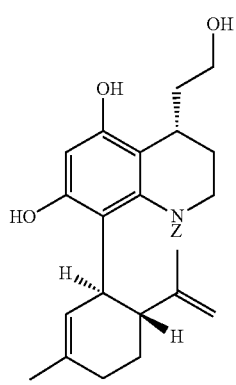
17f
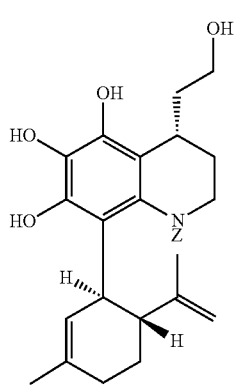
17g
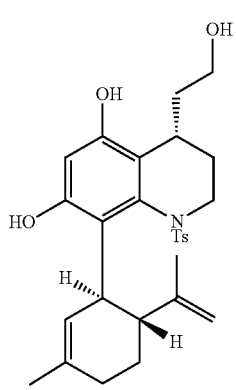
17h
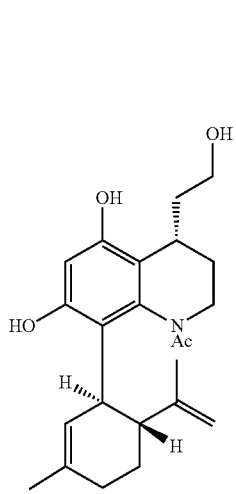
17i
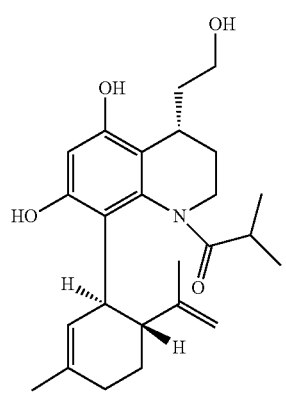
17j
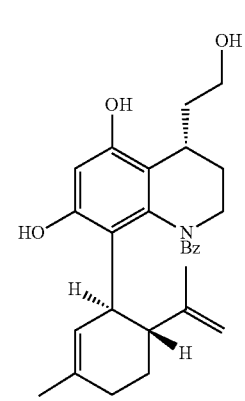
Structures 18a-18j
18a
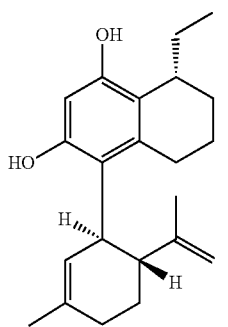
18b
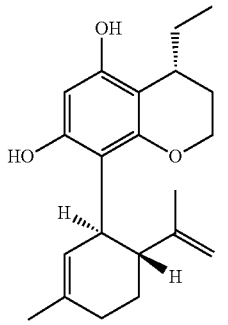

18c
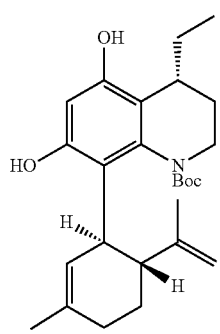
18d
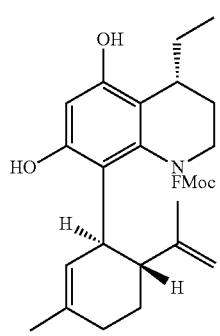
18e
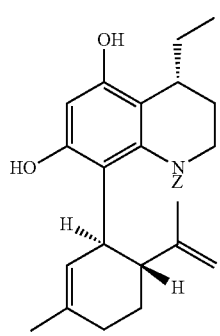
18f
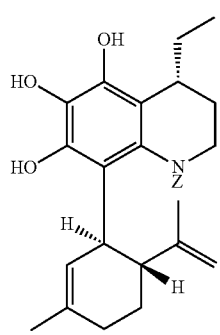
18g
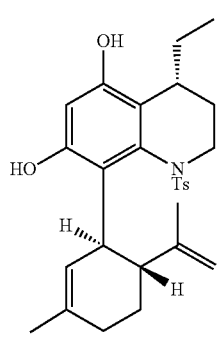
18h
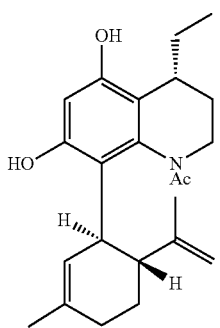
18i
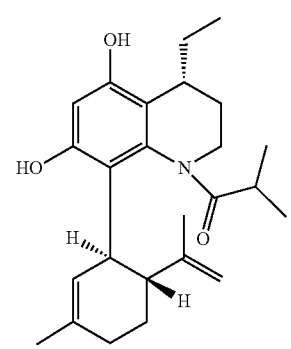
18j
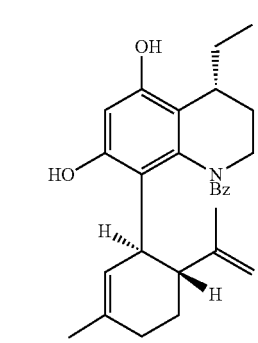
Synthesis of Compounds 19 to 22
Deprotection of 17c to 17j or 18c to 18j produced the compounds 19 to 22 described below.
Structures 19, 20, 21, 22
19
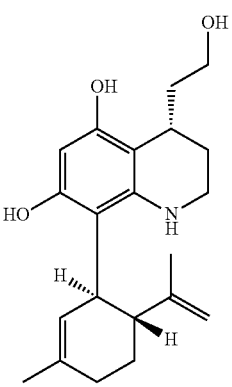

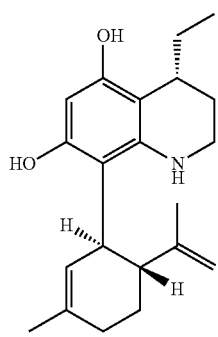

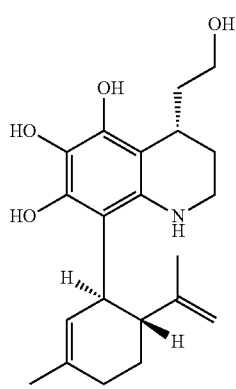

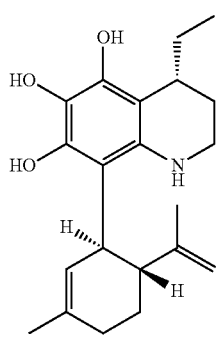

Conclusion

The application of the novel routes of synthesis to produce novel cannabidiol analogues and their intermediates is of benefit.

Compounds of the general formulas I and II are as detailed below and are equivalent to the compounds of structures 11a to 11j (except 11f), 12a to 12j (except 11f), 17a to 17j and 17a to 17j. Such compounds may provide improved or new therapeutic treatment options.

Deprotection of particular compounds has been found to produce additional novel molecules which provide additional improved or new therapeutic benefit. Such compounds include 13, 14, 19, 20, 21 and 22.

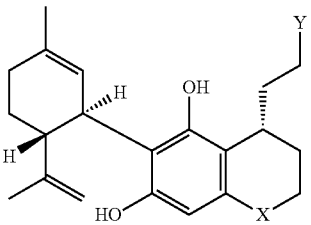

Formula I where X is either $CH_2$; O; NBoc; NFMoc; NZ; NTs; NAc; NC(O)iPr; NBz or NH and Y is either H or OH.

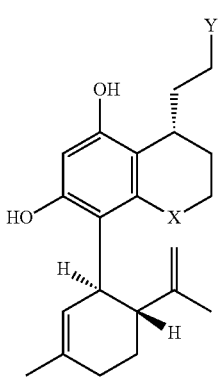

Formula II where X is either $CH_2$; O; NBoc; NFMoc; NZ; NTs; NAc; NC(O)iPr; NBz or NH and Y is either H or OH.

Example 3: Evaluation of Cannabinoid Derivatives for Anticonvulsant Activity using the Maximal Electroshock Seizure Threshold (MEST) Test in the Mouse The efficacy of exemplary cannabinoid derivatives according to Formula I and Formula II were tested in a mouse model of generalised seizure, the maximal electroshock seizure threshold (MEST) test.

The maximal electroshock seizure threshold (MEST) test is widely utilized preclinically to evaluate pro- or anti-convulsant properties of test compounds (Loscher et al., 1991).

In the MEST test the ability of a drug to alter the seizure threshold current required to induce hind limb tonic extensor convulsions is measured according to an "up and down" method of shock titration (Kimball et al., 1957). An increase in seizure threshold is indicative of anti-convulsant effect. Antiepileptic drugs including the sodium channel blockers (e.g. lamotrigine) with clinically proven efficacy against generalised tonic-clonic seizures all exhibit anti-convulsant properties in this test in the mouse.

Conversely, a reduction in seizure threshold is indicative of a pro-convulsant effect as observed with known convulsant agents such as picrotoxin.

The ability of a test compound to alter the stimulus intensity, expressed as current (mA), required to induce the presence of tonic hind limb extensor convulsions, is assessed in the MEST. The outcome of the presence (+) or absence (0) of tonic hind limb extensor convulsions observed from a current to produce tonic hind limb extension in 50% of animals in the treatment group ($CC_{50}$) determines the seizure threshold for the treatment group and the effects were then compared to the $CC_{50}$ of the vehicle control group.

Methods

Study Details

Naïve mice were acclimatised to the procedure room in their home cages for up to 7 days, with food and water available ad libitum.

All animals were weighed at the beginning of the study and randomly assigned to treatment groups based on a mean distribution of body weight across groups. All animals were dosed at 10 mL/kg via intraperitoneal (i.p) injection, with either vehicle, test compound at 200 mg/kg, or diazepam at 2.5 mg/kg.

Animals were individually assessed for the production of a tonic hind limb extensor convulsion at 60 min post-dose for vehicle, 30-120 min post-dose for test compound (dependant on compound) and 30 min post-dose for diazepam, from a single electroshock.

The first animal within a treatment group was given a shock at the expected or estimated $CC_{50}$ current. For subsequent animals, the current was lowered or raised depending on the convulsions outcome from the preceding animal.

Data generated from each treatment group were used to calculate the $CC_{50}$±SEM values for the treatment group.

Test Compounds

Vehicle: (5% ethanol, 5% solutol in 90% Saline) was prepared as follows: 2 mL of ethanol, 2 mL of solutol were warmed to 60° C., in 36 mL of saline (1:1:18).

Positive control: diazepam was used at 2.5 mg/kg.

The test compounds used were 12a, 12b, 18a and 18b. Test compounds were administered at 200 mg/kg (i.p.) in a 1:1:18 ethanol:solutol:saline formulation.

Sample Collection

Each animal was humanely killed immediately after production of a convulsion by destruction of the brain from striking the cranium, followed by the confirmation of permanent cessation of the circulation from decapitation under The Humane Killing of Animals under Schedule 1 to the Animals (Scientific Procedures) Act 1986. Terminal blood and brain collection were performed following decapitation.

Blood was collected in Lithium-heparin tubes and centrifuged at 4° C. for 10 minutes at 1500×g. The resulting plasma was removed (>100 μL) and split into 2 aliquots of 0.5 mL Eppendorf tubes containing 10 μL of ascorbic acid (100 mg/mL) for stabilisation. Brains were removed, washed in saline and halved. Each half was placed into separate 2 mL screw cap cryovials, weighed and frozen on cardice.

Statistical analysis

The data for each treatment group were recorded as the number of +'s and 0's at each current level employed and this information is then used to calculate the $CC_{50}$ value (current required for 50% of the animals to show seizure behaviour)±standard error.

Test compound effects were also calculated as percentage change in $CC_{50}$ from the vehicle control group.

Significant difference between drug-treated animals and controls were assessed according to Litchfield and Wilcoxon (1949).

Results

FIGS. 1 to 4 and Tables 1 to 4 describe the data produced in this experiment.

In the vehicle group, the $CC_{50}$ value was calculated to be 21 mA.

In the diazepam (2.5 mg/kg) treated group, administered i.p. 30 minutes before the test, the $CC_{50}$ value was 35 mA. This result was statistically significant ($p<0.001$) compared to the vehicle control.

In the test compound treatment groups, administered i.p. between 30 and 120 minutes before the test, all four compounds produced a statistically significant $CC_{50}$ value compared to vehicle.

Such data are indicative that these compounds will be of therapeutic benefit.

TABLE 1

Evaluation of effect of Compound 12a in the MEST test

| Treatment | Dose (mg/kg) | Test time post dose (min) | N | $CC_{50}$ +/− SEM | Significance | % change from vehicle |
|---|---|---|---|---|---|---|
| Vehicle | — | 60 | 12 | 21.0 +/− 0.5 | — | — |
| Diazepam | 2.5 | 30 | 12 | 35.0 +/− 1.1 | P < 0.001 | 66% |
| Compound 12a | 200 | 60 | 8 | 54.0 +/− 0.2 | P < 0.001 | 157% |

TABLE 2

Evaluation of effect of Compound 12b in the MEST test

| Treatment | Dose (mg/kg) | Test time post dose (min) | N | $CC_{50}$ +/− SEM | Significance | % change from vehicle |
|---|---|---|---|---|---|---|
| Vehicle | — | 60 | 12 | 21.0 +/− 0.5 | — | — |
| Diazepam | 2.5 | 30 | 12 | 35.0 +/− 1.1 | P < 0.001 | 66% |
| Compound 12b | 200 | 30 | 12 | 43.8 +/− 0.2 | P < 0.001 | 109% |

TABLE 3

Evaluation of effect of Compound 18a in the MEST test

| Treatment | Dose (mg/kg) | Test time post dose (min) | N | $CC_{50}$ +/− SEM | Significance | % change from vehicle |
|---|---|---|---|---|---|---|
| Vehicle | — | 60 | 12 | 21.0 +/− 0.5 | — | — |
| Diazepam | 2.5 | 30 | 12 | 35.0 +/− 1.1 | P < 0.001 | 66% |
| Compound 18a | 200 | 120 | 12 | 41.8 +/− 0.5 | P < 0.001 | 99% |

TABLE 4

Evaluation of effect of Compound 18b in the MEST test

| Treatment | Dose (mg/kg) | Test time post dose (min) | N | CC$_{50}$ +/− SEM | Significance | % change from vehicle |
|---|---|---|---|---|---|---|
| Vehicle | — | 60 | 12 | 21.0 +/− 0.5 | — | — |
| Diazepam | 2.5 | 30 | 12 | 35.0 +/− 1.1 | $P < 0.001$ | 66% |
| Compound 18b | 200 | 120 | 12 | 40.3 +/− 0.8 | $P < 0.001$ | 92% |

Conclusions

These data demonstrate a therapeutic effect for the compounds of Formula I and Formula II.

These data are significant as they provide heretofore unknown evidence that these novel cannabinoid derivatives may be of therapeutic value.

The compounds tested were those detailed as Compound 12a, Compound 12b, Compound 18a and Compound 18b. Such compounds are examples of the cannabinoid derivatives of general Formula I and Formula II.

Clearly as all compounds showed efficacy in the MEST test such therapeutic efficacy can be attributed to the cannabinoid derivatives of general Formula I and Formula II of the invention.

The invention claimed is:

1. A compound of the general Formula I or a salt thereof

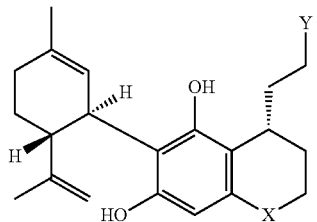

Formula I where X is either $CH_2$; O; NBoc; NFMoc; NZ; NTs; NAc; NC (O)iPr; NBz or NH and Y is either H or OH.

2. A compound of general Formula II or a salt thereof

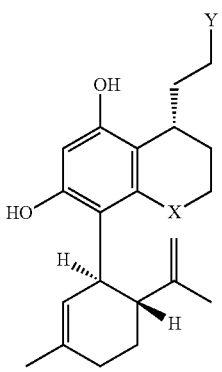

Formula II where X is either $CH_2$; O; NBoc; NFMoc; NZ; NTs; NAc; NC (O) iPr; NBz or NH and Y is either H or OH.

3. A pharmaceutical composition comprising a compound of claim 1 or salt thereof.

4. A pharmaceutical composition as claimed in claim 3, wherein the pharmaceutical composition is selected from a tablet, a capsule, a granule, a powder for inhalation, a sprinkle, an oral solution and a suspension.

5. A pharmaceutical composition as claimed in claim 3, wherein the composition additionally comprises one or more of: an excipient selected among a carrier, an oil, a disintegrant, a lubricant, a stabilizer, a flavouring agent, an antioxidant, a diluent and another pharmaceutically effective compound.

6. A method of treating epilepsy in a mammal in need thereof comprising administering a pharmaceutical preparation comprising a compound of claim 1 or salt thereof.

7. A process for the production of a compound of general Formula I comprising reacting a resorcinol unit of Structure 1a-j via a Friedel-Crafts 1,4-addition to produce compounds of Structures 2a to 2j or 3a to 3j followed by subsequent steps to produce the compounds of general Formula I via intermediates.

8. A compound selected from any one of:

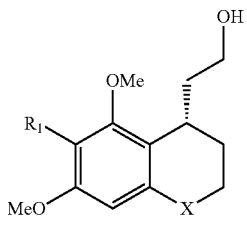

2a-e and 2g-j

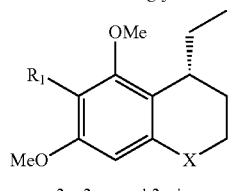

3a, 3c-e and 3g-j

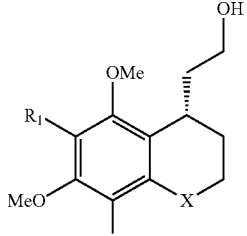

4a-e and 4g-j

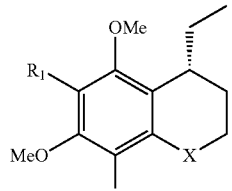

5a-e and 5g-j

-continued

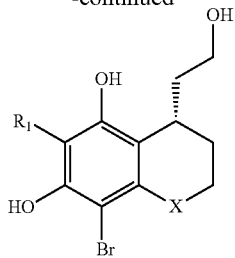

6a-e and 6g-j

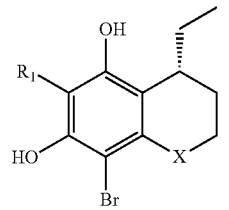

7a-e and 7g-j

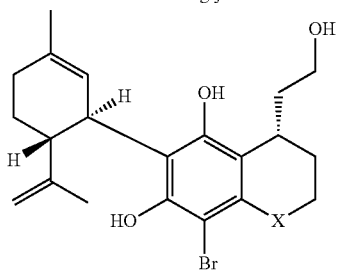

9a-e and 9g-j

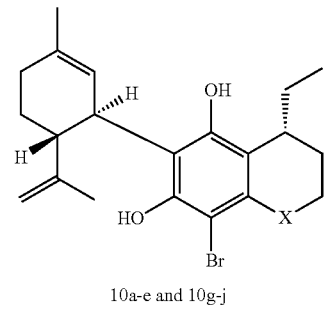

10a-e and 10g-j

-continued

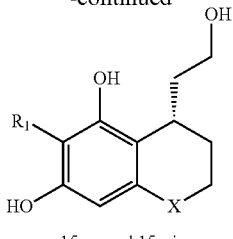

15a-e and 15g-j

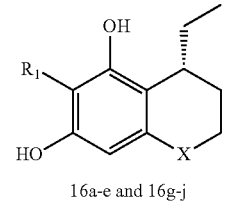

16a-e and 16g-j wherein $R_1$ is H, and
wherein X is selected from any one of $CH_2$, O, NBoc, NFmoc, NZ, NTs, NAc, NC(O)iPr and NBz.

9. A pharmaceutical composition comprising a compound of claim 2 or salt thereof.

10. A pharmaceutical composition as claimed in claim 9, wherein the pharmaceutical composition is selected from a tablet, a capsule, a granule, a powder for inhalation, a sprinkle, an oral solution and a suspension.

11. A pharmaceutical composition as claimed in claim 9, wherein the composition additionally comprises one or more of: an excipient selected among a carrier, an oil, a disintegrant, a lubricant, a stabilizer, a flavouring agent, an antioxidant, a diluent and another pharmaceutically effective compound.

12. A method of treating epilepsy in a mammal in need thereof comprising administering a pharmaceutical preparation comprising a compound of claim 2 or a salt thereof.

13. A process for the production of a compound of general Formula II comprising reacting a resorcinol unit of Structure 1a-j via a Friedel-Crafts 1,4-addition to produce compounds of Structures 2a to 2j or 3a to 3j followed by subsequent steps to produce the compounds of general Formula II via intermediates.

* * * * *